United States Patent
Lo et al.

Patent Number: 5,662,144
Date of Patent: Sep. 2, 1997

[54] EASY CLAMP TUBING AND A METHOD FOR CLAMPING THE TUBING

[75] Inventors: Ying-Cheng Lo, Green Oaks; Sanjay V. Odak, Grayslake; Rafael A. Castellanos, Roselle, all of Ill.

[73] Assignee: Baxter Healthcare Corporation, Deerfield, Ill.

[21] Appl. No.: 588,216

[22] Filed: Jan. 18, 1996

Related U.S. Application Data

[63] Continuation of Ser. No. 320,359, Oct. 11, 1994, abandoned.

[51] Int. Cl.⁶ .................................................. F16L 11/04
[52] U.S. Cl. ...................................... 138/119; 138/177
[58] Field of Search .............................. 138/119, 177, 138/178; 251/4, 7

[56] References Cited

U.S. PATENT DOCUMENTS

| | | | |
|---|---|---|---|
| 3,260,412 | 7/1966 | Larkin | 138/119 X |
| 3,508,587 | 4/1970 | Mauch | 251/4 |
| 3,720,235 | 3/1973 | Schrock | 138/119 |
| 3,733,046 | 5/1973 | Press | 251/4 |
| 3,770,023 | 11/1973 | Rink | |
| 3,811,649 | 5/1974 | Press et al. | |
| 4,131,399 | 12/1978 | Calvet | 138/119 X |
| 4,257,422 | 3/1981 | Duncan | 138/119 X |
| 4,424,832 | 1/1984 | Koda | 251/4 |
| 4,575,041 | 3/1986 | Hu | 251/4 |
| 4,690,162 | 9/1987 | Lyddy et al. | 251/4 |
| 5,215,450 | 6/1993 | Tamari | 138/119 |

FOREIGN PATENT DOCUMENTS

| | | | |
|---|---|---|---|
| 1234912 | 5/1960 | France | 138/119 |
| 2 321 655 | 8/1976 | France | |
| 1222065 | 2/1971 | United Kingdom | 138/119 |
| 2 109 088 | 5/1983 | United Kingdom | |
| WO91/08098 | 6/1991 | WIPO | |

*Primary Examiner*—Patrick Brinson
*Attorney, Agent, or Firm*—Thomas S. Borecki; Charles R. Mattenson; Robert M. Barrett

[57] ABSTRACT

A tubing has members located on the inside surface of a tubing. The flow through the tubing is completely occluded when the tubing is clamped due to the members filling channels around the clamped site. Reduced clamping pressure is required to fully occlude the flow through the tubing. The tubing undergoes less deformation upon clamping and returns to its pre-clamped form upon recovery.

13 Claims, 1 Drawing Sheet

EASY CLAMP TUBING AND A METHOD FOR CLAMPING THE TUBING

This is a continuation of application Ser. No. 08/320,359, filed on Oct. 11, 1994 now abandoned.

BACKGROUND OF THE INVENTION

The present invention generally relates to an apparatus and a method for occluding flow in a tubing. More specifically, the present invention relates to an easy-to-clamp tubing.

In a variety of industries, and for a variety of applications, tubing or other conduit is required to transport fluid or non-fluid substances and gases between two points. In many situations, it is desirable to stop the flow of fluid through the tube. This can be accomplished, if a flexible tube is being used, by using a clamp or other fluid occluder.

One art in which flexible tubing is used, is the medical arena. It is generally known that a tubing, a catheter or the like may be used to deliver fluids, nutrition, medicine, aerosols and gases to a patient and/or to remove body fluids from a patient. For example, in peritoneal dialysis, a tubing or a catheter is used to introduce a dialysis solution into the peritoneal cavity. After solutes are exchanged between the dialysate and the blood, the dialysis solution is simply drained from the body cavity through the tubing or the catheter.

To control fluid flow during a medical procedure, it is known to use clamps. The clamps are designed to compress the interior walls of the flexible tubing against each other. Such clamps include, for example, roller clamps and hemostats. For example, during delivery of medicaments to a patient, it is known to use a roller clamp to terminate the flow of, for example, an intravenous fluid to the patient.

At least three requirements arise with respect to the clamping of a length of tubing to occlude flow therethrough. One requirement is the avoidance of leaks at the point of clamping. Another requirement is that the necessary clamping pressure to effectively occlude the tubing is low enough for a patient/user with compromised strength to perform same. A further requirement is that occlusion occurs without crushing the center of the tubing.

Conventional tubing, when in a fully clamped position, still may provide incomplete occlusion. In this regard, open channels at the end portions of the clamped area can be created. These open channels allow fluid to leak through the intended occlusion. Although by applying sufficient pressure these open channels can be closed, this requires the application of significant pressure to fully engage the clamp.

However, one of the issues in an out-patient care setting is insuring that an out-patient can successfully manage certain procedures. The clamping of a tube is one such procedure that the out-patient should be able to perform. In order to perform this procedure, it is necessary to have a reduced clamp pressure requirement to fully occlude the flow through the tubing. Therefore, it may not be possible to provide a clamp that will insure total occlusion that can be used by patients who are weak or otherwise infirm.

A further problem that arises is that if too much pressure is applied to the tube after the clamp is removed, it may not regain its original shape. This may create problems if occlusion of fluid flow through the tube is only temporary.

Accordingly, a need exists for improved tubing that can be easily clamped resulting in a fully occluded tubing.

SUMMARY OF THE INVENTION

The present invention provides improved tubing that can easily be clamped and a method for clamping the tubing. The tubing includes means located on an interior wall for insuring that the tubing, when clamped, is completely occluded.

To this end, in an embodiment, the present invention provides a conduit for allowing flow of a fluid therein comprising a tubing having an interior. At least one member is located on the interior of the tubing. The member is so constructed and arranged to occlude the flow of fluid through the interior during compression of the tubing.

In a preferred embodiment, a first and second member are provided.

In an embodiment, the first member and the second member are located symmetrically about a vertical axis in the center of the tubing.

In an embodiment, the first member and the second member of the conduit are teardrop-shaped.

In an embodiment, the first member and the second member of the conduit are constructed from plastic.

In an embodiment, the first member and the second member of the conduit are constructed and arranged on the interior of the tubing for the length of the tubing.

In an embodiment, the first member and the second member are located symmetrically diagonal about the vertical axis in the center of the tubing.

The invention also provides a method for occluding flow comprising the steps of: providing a hollow tubing having interior walls; providing a first member and a second member on the interior walls; and compressing the tubing to occlude flow through the tubing.

In an embodiment, the method further comprises the steps of placing a clamp around the tubing and squeezing the tubing with the clamp.

Additionally, the present invention provides a method for making a fluid conduit capable of being occluded comprising the steps of providing a length of tubing having an interior; providing means on the interior of the tubing that will prevent any open channels when the tubing is occluded.

In an embodiment, the method further comprises the step of locating the first member opposite from the second member on the interior of the tubing.

In an embodiment, the first member and the second member extend for at least a portion of the length of the tubing.

The present invention further provides a fluid conduit for a medical tubing comprising a medical grade tubing having an interior wall. The medical grade tubing has a clamped position and an unclamped position. The fluid conduit has a first member and a second member on the interior wall constructed and arranged to provide fluid flow through the tubing when in the unclamped position and no fluid flow through the tubing when the tubing is in the clamped position.

It is, therefore, an advantage of the present invention to provide an improved conduit for occluding fluid flow.

Another advantage of the present invention is to provide an improved method of occluding flow.

A further advantage of the present invention is to provide an improved tubing for peritoneal dialysis applications.

A still further advantage of the present invention is to provide complete occlusion and eliminate leaking at the clamping site, due to the members located on the interior walls of the tubing.

An additional advantage of the present invention is to provide an improved method for making a fluid conduit capable of being occluded.

Yet another advantage is to provide an improved tubing that has unimpaired flow characteristics requiring reduced clamping pressure.

Still further, an advantage of the present invention is to provide an improved tubing that is less likely to experience alterations of shape caused by pressure. The tubing easily returns to its original form after pressure, such as clamping, is applied. Therefore, occlusion can be achieved in the present invention without having deformation following the clamping of the tubing.

Moreover, an advantage of the present invention is to provide tubing for use in any medical procedure requiring a catheter or tubing.

Additional features and advantages of the present invention are described in and will be apparent from the detailed description of the presently preferred embodiments and from the drawings.

DETAILED DESCRIPTION OF THE PRESENTLY PREFERRED EMBODIMENTS

The present invention provides a tubing and a method of clamping the same. Pursuant to the present invention, in an embodiment, the tubing includes means located on the inside surface of the tubing that prevent open channels from forming in the tube when the tube is clamped.

Although in the preferred embodiment the tubing is designed for medical applications, it should be appreciated that the tubing of the present invention can be used in a variety of industries.

Figure 1:
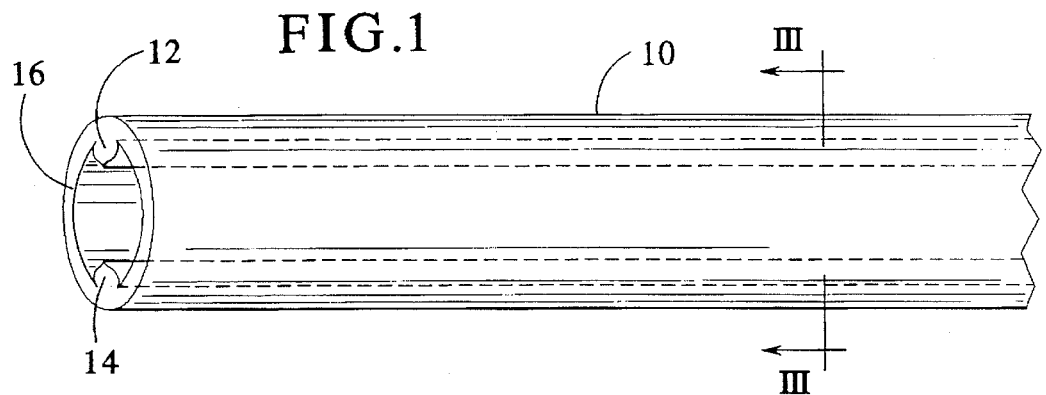
FIG. 1 illustrates a perspective view partially in cross-section of an embodiment of the present invention illustrating two elongated members extending for the length of the tubing.

Referring now to the drawings, FIG. 1 illustrates a tubing 10 having a first member 12 and a second member 14 located on an interior wall 16 of the tubing 10. Although in the preferred embodiment two members are illustrated, more than two members or less than two members can be provided.

Although in the preferred embodiment illustrated the first member 12 and the second member 14 extend for the length of the tubing 10, the members 12 and 14 may extend for only a portion along the inside surface of the tubing. For example, a finite portion of the tubing 10 may be provided with the members 12 and 14 resulting in a bead-like formation on the interior surface of the tubing 10. The bead-like formations or any finite portions are located substantially equidistant from a vertical line in the center of the tube and are diagonally symmetrical. As a result, the tubing 10 may be occluded by squeezing or clamping at the point of 90° to one of the bead-like formations or other finite portions.

The tubing 10 is preferably constructed from a flexible material, such as polyvinyl chloride. Of course, other materials may be used to provide a flexible tubing 10 incorporating the clamping feature of the present invention.

Figure 2:
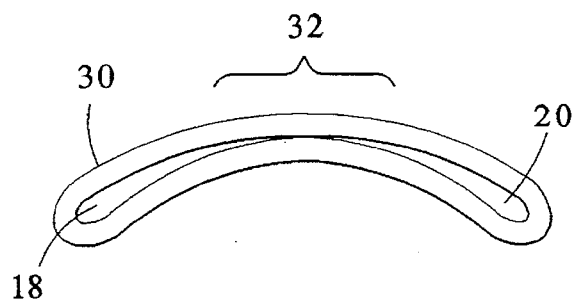
FIG. 2 illustrates a cross-sectional view of conventional tubing having incomplete occlusion of its flow through the tubing following clamping due to the open channels that allow leaks to form.
Figure 3:
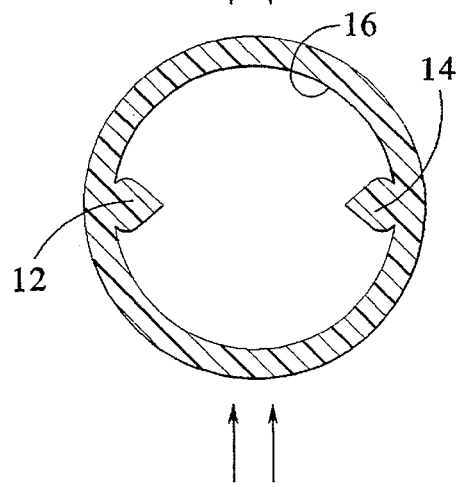
FIG. 3 illustrates a cross-sectional view taken generally along the line III—III of FIG. 1.

The members 12 and 14 are provided within the tubing 10 such that when pressure is applied to the tubing 10, as illustrated by the arrows in FIG. 3, the interior of the tubing 10 occludes flow of a fluid through the tubing 10. Therefore, as opposed to prior tubing, those portions of a conventional tubing 30 (see FIG. 2) illustrated by channels 18 and 20 are filled by the members 12 and 14 at the point of clamping to completely occlude flow through the tubing 10. Conventional tubing 30, on the other hand, may allow seeping or leaking of fluids through the tubing 30 at the point of clamping such that fluids pass through the channels 18 and 20.

It has been found that the clamping pressure required to completely occlude the flow through the tubing 10 is approximately 80% of that pressure normally needed for clamping of conventional round cross-section tubing. It should be appreciated that any means can be used to clamp the tubing of the present invention. The means for clamping the tubing 10 can include, but is not limited to, manually squeezing or pressing a clamp over the tubing 10 or using a twisting method whereby two hands are used to twist the clamp around the tubing 10. The twisting action turns the tubing 10, occludes the tubing 10 and locks the tubing 10 in a closed position whereby the flow is occluded.

An additional advantage of the present invention is that, due to the structure and the flexibility of the tubing 10, the tubing 10 quickly recovers to its pre-clamped form without deformation upon releasing of the clamp or other pressure exerted to the walls of the tubing 10.

In FIG. 2, as previously discussed, the conventional tubing 30 is illustrated in the clamped position showing the channel 18 and the channel 20. The channels 18 and 20 are formed from the clamping pressure or other pressure applied to the wall of the tubing 30. However, due to formation of the channels 18 and 20, fluids attempting to be occluded through the tubing 30 are allowed to leak or otherwise pass through an intended occluded site 32. Leakage through the occluded site 32, therefore, occurs when the conventional tubing 30 is squeezed or pressure is otherwise applied because the channels 18, 20 are not filled or blocked by present clamping methods thereby completely preventing flow.

Referring now to FIG. 3, in an embodiment, the tubing 10 is provided having an interior 16, the first member 12 and the second member 14. As previously set forth, the members 12 and 14 may extend for a finite portion within the length of the tubing 10. The finite portion may be of such a length that the members 12, 14 represent beads within the tubing 10. The first member 12 and the second member 14, in a preferred embodiment, are teardrop-shaped in cross-section and may be constructed from plastic. The arrows shown in FIG. 3 indicate the direction of squeezing or clamping of the tubing 10.

When the tubing 10 is squeezed by a person to effect clamping, the channel 18 and the channel 20, that can be open in conventional tubing, are occupied with the members 12, 14. Therefore, any leaks through the clamped tubing 10 are prevented.

Figure 4:
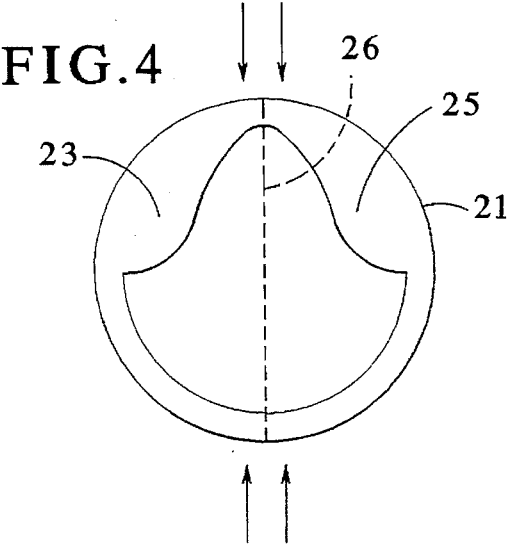
FIG. 4 illustrates a cross-sectional view of an embodiment of a tubing of the present invention with two members located along the inside surface of the tubing symmetrically about a vertical line in the center of the tubing.

In FIG. 4, as illustrated, an alternate embodiment of a tubing 21 of the present invention is shown. A first member 23 and a second member 25 may be located symmetrically about a vertical line 26 in the center of the tubing 21. The members 23, 25 may be a part of elongated members that continue for the length of the tubing 21 or may be a finite portion thereof forming bead-like formations in the length of tubing 21 at points in the tubing 21 substantially equidistant from the ends of the tubing 21. Likewise, the first and second members 23 and 25 may be a single integral member rather than two separate members.

To occlude the tube 21 of FIG. 4, the tubing can be clamped. The arrows in FIG. 4 indicate the direction to squeeze or clamp the tubing 21 to effect occlusion of the tubing 21.

Figure 5:
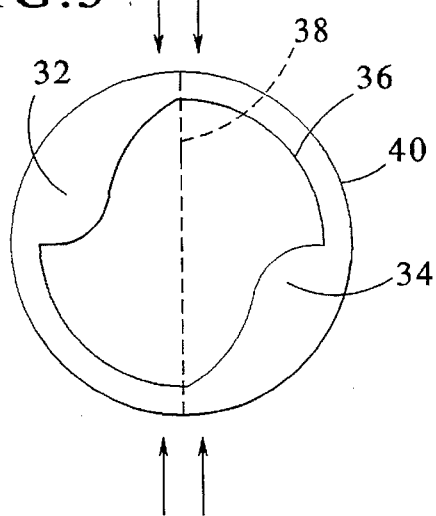
FIG. 5 illustrates a cross-sectional view of an embodiment of a tubing of the present invention with two teardrop-shaped beads located on the inside surface of the tubing diagonally symmetrical about a vertical line in the center of the tubing.

Alternatively, as shown in FIG. 5, a first member 32 and a second member 34 may be located on an inside surface 36 of a tubing 40 diagonally symmetrical about a vertical line 38 in the center of the tubing 40. In an embodiment, the first member 32 runs for the length of the tubing 40 and the second member 34 runs for the length of the tubing 40. Of course, as discussed previously with reference to the embodiments illustrated in FIGS. 1, 3 and 4, the members 32, 34 may extend for any finite portion within the length of the tubing 40 including bead-like formations at points substantially equidistant from ends of the tubing 40.

The members of all of the embodiments illustrated in FIGS. 1 and 3–5 or any finite portions thereof may be integrally formed with the wall of the tubing itself. In this way, the tubing wall is shaped, during manufacture thereof, to form the member on its inside surface. Alternatively, the member may be added to a pre-existing length of tubing by methods known in the art.

By way of example, and not limitation, the flexible tubing can be used for a number of medical procedures including: nasogastric enteral feeding; intravenous therapy; and dialysis procedures.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

We claim:

1. A conduit for allowing the flow of a fluid therein, the conduit comprising:

a flexible tubing having a length defined by an interior that is defined by interior walls;

means located on the interior wall of the tubing for occluding the flow of fluid through at least portions of the interior during compression of at least a portion of the tubing wherein the means for occluding includes a first member and a second member wherein the first member and the second member are integrally formed with the interior wall at points symmetrically diagonal and entirely between a quadrant defined by a vertical axis perpendicular to the length of the tubing and a horizontal axis perpendicular to the length of the tubing and perpendicularly displaced from the vertical axis and further wherein each of the first member and the second member form only a single S-curve across an entire length of the interior wall within their respective quadrants.

2. The conduit of claim 1 wherein the first member and the second member are constructed from plastics.

3. The conduit of claim 1 wherein the first member and the second member are constructed and arranged on the interior of the tubing for the length of the tubing.

4. A method for making a fluid conduit capable of being occluded, the method comprising the steps of:

providing a length of tubing having an interior;

providing a first member;

providing a second member wherein the first member and the second member are integrally formed with the interior of the tubing; and locating the first member and the second member symmetrically diagonally situated and entirely between a quadrant defined by a vertical axis perpendicular to the length of the tubing and a horizontal axis perpendicular to the length of the tubing and perpendicularly displaced from the vertical axis and further wherein each of the first member and the second member form only a single S-curve across an entire length of the interior wall within their respective quadrants.

5. The method of claim 4 further comprising the step of:

constructing the tubing from a flexible material.

6. The method of claim 5 wherein the flexible material is polyvinyl chloride.

7. The method of claim 4 wherein the first member and the second member extend for at least a portion of the length of the tubing.

8. The method of claim 4 wherein the first member and second member extend for the length of the tubing.

9. A fluid conduit for a medical tubing comprising:

a medical grade tubing having a length defined by an interior wall, the medical grade tubing having a clamped position and an unclamped position; and a first member and a second member on the interior wall, the first member and the second member constructed and arranged to provide fluid flow through the tubing when in the unclamped position and to prevent fluid flow through the tubing when the tubing is in the clamped position wherein the first member and the second member are symmetrically diagonally situated and located entirely between a quadrant defined by a vertical axis perpendicular to the length of the tubing and a horizontal axis perpendicular to the length of the tubing and perpendicularly displaced from the vertical axis and further wherein each of the first member and the second member form only a single S-curve across an entire length of the interior wall within their respective quadrants.

10. The fluid conduit of claim 9 wherein the medical grade tubing is constructed from a flexible material.

11. The fluid conduit of claim 9 wherein the first member and the second member extend for the length of the tubing.

12. A fluid conduit comprising:

a tubing having a length defined by an interior wall; and at least a first member and a second member on the interior wall, the first member and the second member constructed and arranged to provide fluid flow through the tubing when in an unclamped position and having no fluid flow through the tubing when the tubing is in a clamped position wherein the first member and the second member are symmetrically diagonally situated and located entirely between a quadrant defined by a vertical axis perpendicular to the length of the tubing and a horizontal axis perpendicular to the length of the tubing and perpendicularly displaced from the vertical axis and further wherein each of the first member and the second member form only a single S-curve across an entire length of the interior wall within their respective quadrants.

13. The fluid conduit of claim 12 wherein the first member and the second member extend for the length of the tubing.

* * * * *